(12) United States Patent
Fry

(10) Patent No.: US 11,810,448 B2
(45) Date of Patent: Nov. 7, 2023

(54) SYSTEM AND METHOD FOR MONITORING THE HEALTH OF A USER

(71) Applicant: The Government of the United States of America, as represented by the Secretary of Homeland Security, Washington, DC (US)

(72) Inventor: Mark Fry, Marco Island, FL (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 0 days.

(21) Appl. No.: 17/834,437

(22) Filed: Jun. 7, 2022

(65) Prior Publication Data

US 2023/0177947 A1    Jun. 8, 2023

Related U.S. Application Data

(60) Provisional application No. 63/285,318, filed on Dec. 2, 2021.

(51) Int. Cl.
| | |
|---|---|
| *G08B 25/01* | (2006.01) |
| *G16H 40/67* | (2018.01) |
| *A61B 5/00* | (2006.01) |
| *A61B 5/0205* | (2006.01) |

(52) U.S. Cl.
CPC .......... *G08B 25/016* (2013.01); *A61B 5/0022* (2013.01); *A61B 5/02055* (2013.01); *A61B 5/742* (2013.01); *A61B 5/746* (2013.01); *G16H 40/67* (2018.01)

(58) Field of Classification Search
CPC .............................. G08B 21/02; H04M 3/5116
USPC ........................................................ 340/573.1
See application file for complete search history.

(56) References Cited

U.S. PATENT DOCUMENTS

| | | | |
|---|---|---|---|
| 9,675,875 B2 | 6/2017 | Dugan et al. | |
| 9,993,195 B2 | 6/2018 | Van Vugt et al. | |
| 10,955,919 B2 | 3/2021 | Joo | |
| 2010/0260325 A1* | 10/2010 | Clawson ................ | G16H 40/20 379/45 |
| 2014/0118140 A1* | 5/2014 | Amis ...................... | G08B 25/08 340/539.13 |
| 2016/0094967 A1* | 3/2016 | Sulaiman .............. | H04W 76/50 455/404.2 |

(Continued)

*Primary Examiner* — Fabricio R Murillo Garcia
(74) *Attorney, Agent, or Firm* — Lavanya Ratnam; Robert W. Busby; Kelly G. Hyndman

(57) ABSTRACT

A health monitor for monitoring the health a user. The system may comprise an edge computing device, a computer, and a health monitor. The health monitor may comprise a sensor module connected to one or more sensors. The health monitor may comprise a data storage logic configured to store the sensor data. The computer may comprise an emergency dispatch module configured to contact an emergency dispatch system; and a healthcare contact module configured to contact a healthcare provider. The health monitor may comprise a command module configured to receive third party contact information; a biographic intake module configured to receive biographic information about the user; and a third-party contact module configured to send a message to a third party; said message comprising sensor module data and the biographic information of the user.

28 Claims, 13 Drawing Sheets

(56) References Cited

U.S. PATENT DOCUMENTS

| | | | |
|---|---|---|---|
| 2016/0174913 A1* | 6/2016 | Somanath | A61B 5/747 |
| | | | 600/301 |
| 2017/0064572 A1* | 3/2017 | Subramanian | H04W 40/02 |
| 2018/0053401 A1* | 2/2018 | Martin | H04L 67/10 |
| 2020/0163619 A1 | 5/2020 | Lee et al. | |
| 2021/0409412 A1* | 12/2021 | Mohamed | H04L 63/101 |

* cited by examiner

SYSTEM AND METHOD FOR MONITORING THE HEALTH OF A USER

CROSS REFERENCE

This application claims priority to U.S. Provisional 63/285,318 filed on Dec. 2, 2021, the contents of which are incorporated by reference in their entirety.

STATEMENT OF GOVERNMENT INTEREST

The present invention was made by employees of the United States Department of Homeland Security (DHS) in the performance of their official duties. The U.S. Government has certain rights in this invention.

FIELD

Embodiments disclosed herein generally relate to artificial intelligence (AI) based detection and classification for electromagnetic screening processes.

BACKGROUND

There are many types of sensors for measuring variables associated with human performance. US Patent Publication: 2020/0163619 (incorporated by reference in its entirety) discloses a heart rate detector configured to detect heart rate data of the user, an activity sensor configured to detect motion of the user, and a processor. The processor is configured to identify a start of an activity by the user using the motion detected by the activity sensor. U.S. Pat. No. 9,675,875 (incorporated by reference in its entirety) discloses systems and methods for providing biofeedback information (heart rate, pulse rate, temperature, respiration, acceleration, skin resistivity, etc.) to a cellular telephone and for using such information.

Other sensors have been invented that can measure environmental factors such as temperature and humidity. U.S. Pat. No. 10,955,919 (incorporated by reference in its entirety) discloses such a sensor.

There are sensors for measuring sleep patterns such as U.S. Pat. No. 9,993,195 (incorporated by reference in its entirety) The invention relates to a sleep disturbance monitoring apparatus (1) for monitoring a sleep disturbance of a person. An ambience disturbance profile, which describes which levels and/or changes of an ambient signal, which is, for example, a temperature signal or a noise signal, are related to disturbed sleep, is amended depending on a correlation between the ambience signal and a sleep signal which is indicative of the quality of the sleep of the person.

SUMMARY

A system for monitoring a user is disclosed. The system may comprise an edge computing device comprising an operating system, a first network interface, and a software application; a computer comprising a second network interface configured to receive information from the edge computing device; and a health monitor. The health monitor may comprise a processor for executing computer readable instructions; a memory containing tangible non-transitory memory containing computer readable instructions. Said instructions may be configured to cause the processor to execute one or more health applications. The health monitor may comprise a network interface configured to send and receive transmissions with a computer. The sensor module may comprise one or more sensors for receiving sensor data. The health monitor may comprise a data storage logic configured to electronically store sensor data in a data storage device. The health monitor may comprise a data access module configured to retrieve information from the data storage device. The health monitor may comprise a housing configured to physically store one or more of the processor, memory, network interface, sensor module, data storage device, data storage logic, and data access module.

DETAILED DESCRIPTION

Figure 1:
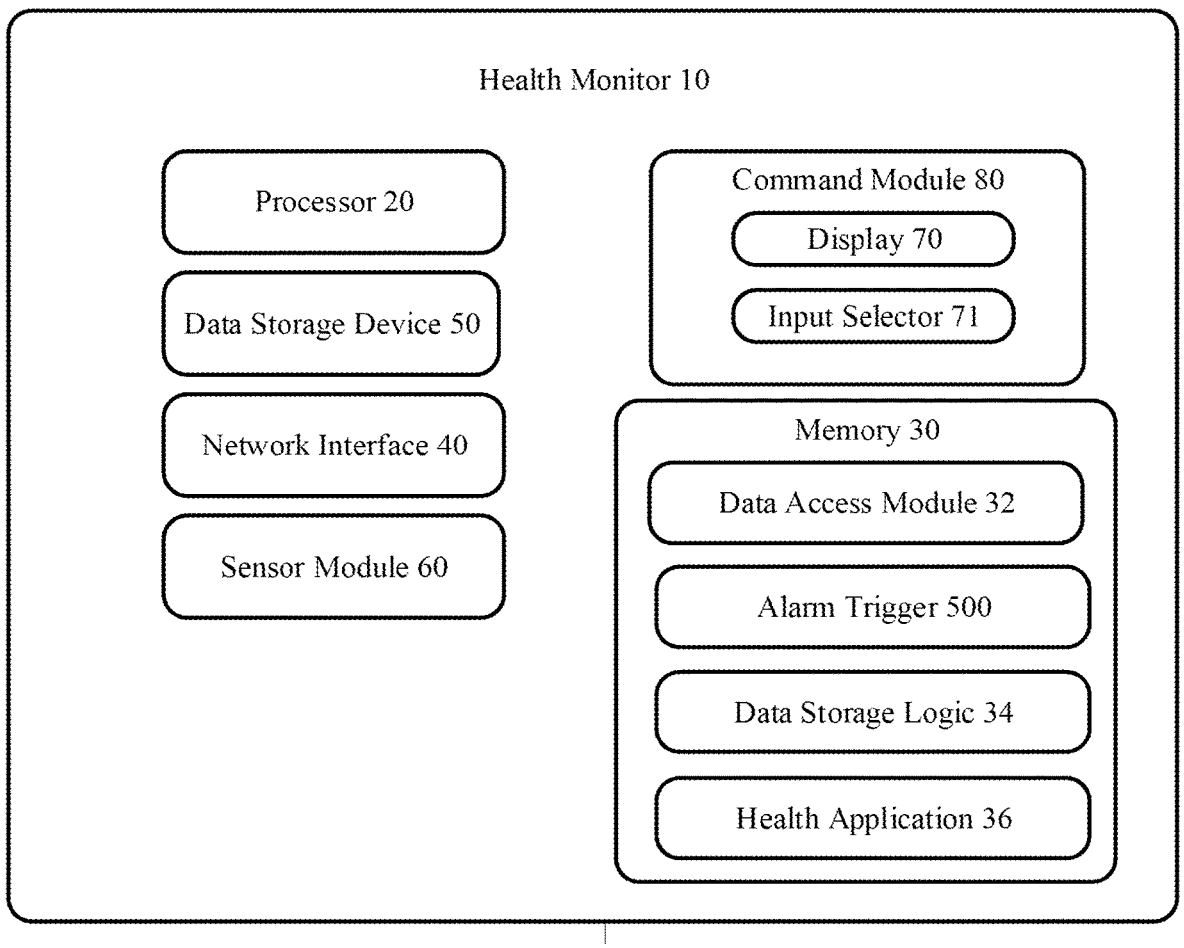
FIG. 1 depicts a health monitor, edge computing device, and a computer.
Figure 1:
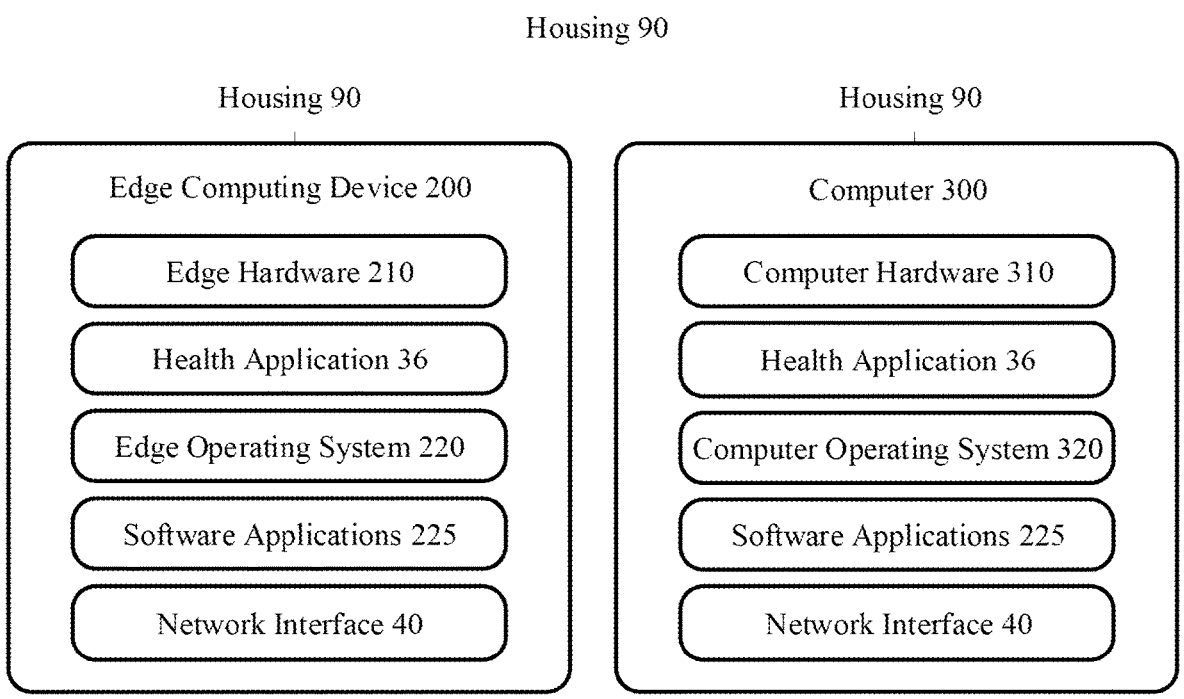

FIG. 1 illustrates a functional block schematic of a health monitor 10. The health monitor may be a wearable such as a watch, band, earphone, ring, glasses, implant, or other device configured to attach or physically connect to a wearer. For example, wearable computers may be attached a human's hand, finger, wrist, head, ankle, or ear. The health monitor may also be an implantable computer.

The health monitor 10 may comprise a processor 20, memory 30, network interface 40, data storage device 50, a sensor module 60, a graphic user interface 70, command module 80, and a housing 90. A housing may be a case surrounding a substantial part or all of the electronic and computer parts of a device. Housings may be made of any suitable materials such as plastic, fiberglass, or metal. The memory 30 may comprise instructions for the processor of the health monitor 10 to create an instance of, run, and/or execute one or more health applications 36. A health application 36 may be a specially designed program, software, or computer application designed to process data, communicate with another health monitor, edge computing device or computer, transmit messages, provide a command module to allow a user to view and input data and decisions, etc. The health application 36 may also run a data access module 32, data storage logic 34, a health application 36, and an alarm trigger 500. In some configurations, the health monitor 10 may be connected to an edge computing device and/or a computer 300. In some configurations, the health monitor 10 is configured to communicate with the edge computing device 200 and the edge computing device is configured to communicate with the computer 300. In some configurations, the health monitor 10 is not configured to communicate with the computer 300 directly.

The command module 80 may comprise an input selector 71, touchscreen, and/or mechanical (buttons, switches, dials, etc.) The command module may comprise a display 70 such as an LCD, multi-touch, or LED screen. The command module 80 may comprise its own microprocessor or be controlled by the processor of the containing device (health monitor, edge computing device, computer.) The display of the command module may be configured to display a graphic user interface for presenting the user with a menu or selection interface to request the user select what sensor module data to share with the computer.

Figure 2:
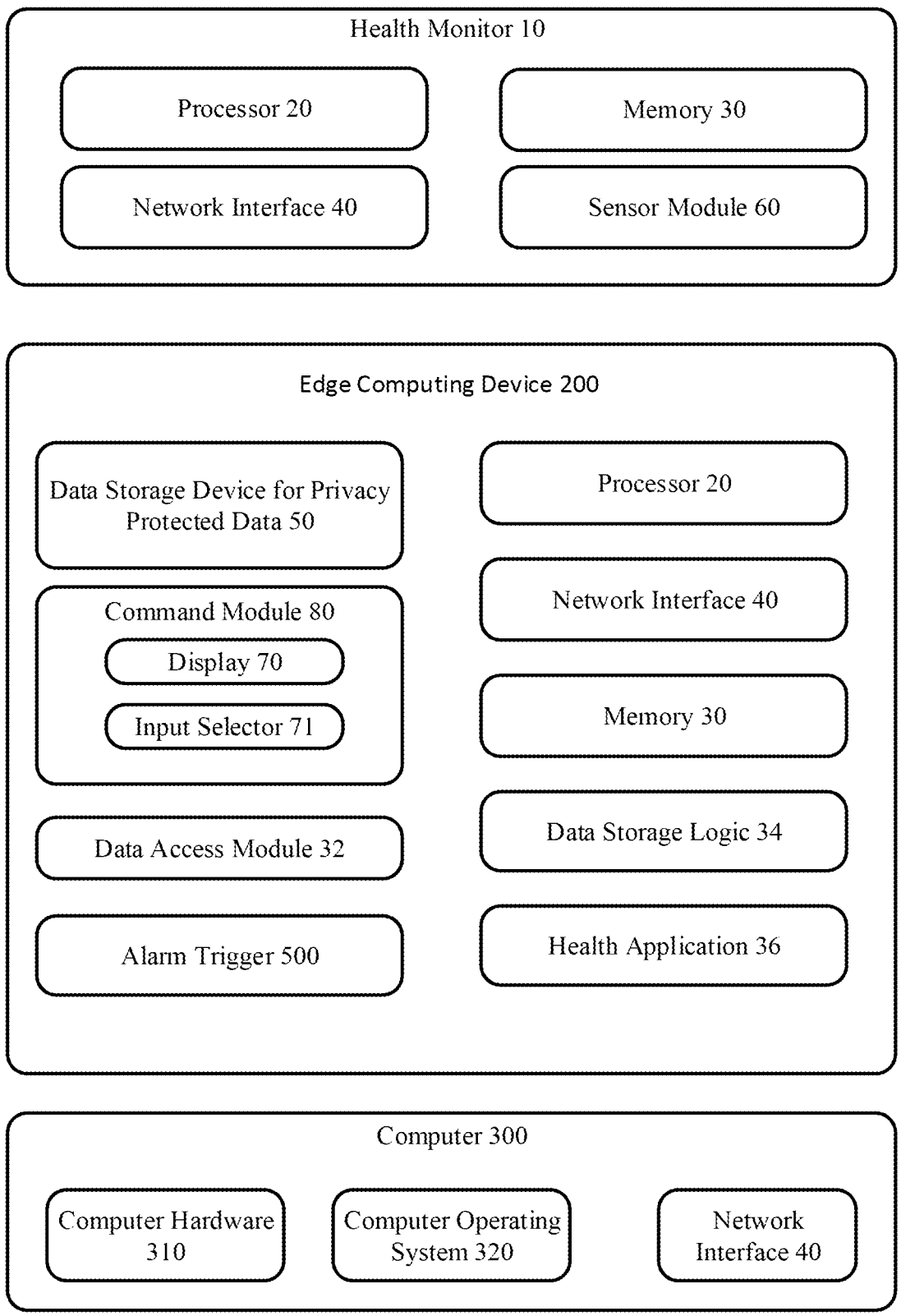
FIG. 2 depicts an alternate configuration of a health monitor, edge computing device, and a computer.

FIG. 2 also shows a health monitor 10, edge computing device 200, and a computer 300. FIG. 2 depicts a health monitor with fewer components and an edge computing device as compared to FIG. 1. In some configurations, both the edge computing device 200 and health monitor 10 will each have a copy of many of the components shown in FIG. 2 (e.g. command module, alarm trigger, etc.) The health monitor 10 may comprise various configurations of hardware and software. The health monitor may be connected to an edge computing device 200.

An edge computing device may be any portable computing device such as a tablet, smartphone, laptop, car computer, second wearable computer, etc. The edge computing device 200 can be a smart phone such as an Apple iPhone. The edge computing device can have an operating system 220 such as Apple IOS, it may include one or more software applications 225 (apps), and it may comprise a housing.

The computer 300 may be a desktop computer, laptop, server, system of networked computers, cloud-based processing platform, etc. The computer 300 may comprise an operating system such as Microsoft Windows or Linux, it may contain one or more software application, and it may comprise a housing. The computer may comprise a network interface 40 configured to contact a healthcare provider and/or a health dispatch system. In some configurations, the health monitor may be configured to contact a healthcare provider and/or health dispatch system without interfacing with a computer 300 or edge computing device 200.

The health monitor 10, edge computing device 200, and computer 300 may have hardware components such as processors, microprocessors, sensors, communication ports, transceivers, power supplies, motherboards, system buses, system memory, data storage, etc. The health monitor 10 may comprise a sensor module 60. The sensor module 60 may comprise or be connected to one or more sensors 61. For example, the sensor 61 may be a vital sensor such as a PPG (photoplethysmography) sensor for measuring blood flow, blood oxygen sensor, heart rate sensor, a skin temperature sensor, or other sensor configured to measure a vital signal from a human body. The sensor module 60 may comprise or be connected to an environmental sensor configured to measure ambient temperature, light, ambient sound decibels, humidity, air quality index, or other sensor configured to measure environmental information related to the position of the health monitor. The sensor module 60 may comprise or be connected to a position sensor such as a GPS, IMU, accelerometer, altimeter or other sensor configured measure position or location information about the health monitor or person using it. The sensor module may comprise or be connected to a data feed configured to receive data from an external source such as time, date, upcoming weather conditions, etc. The sensor module may comprise or be connected to a sleep sensor for measuring sleep quality and duration. The sensor module may comprise or be connected to a plurality of sensors such as a data feed, GPS, blood oxygen sensor, and a heart rate sensor. The health monitor may comprise or be connected to a plurality of sensor modules each comprising different or the same sensors. The one or more sensors may be located physically inside the health monitor 10 or they may be electronically connected to the health monitor via a communication protocol.

The health monitor 10 may comprise a network interface. A network interface may comprise a transceiver, ports, wireless communication, Bluetooth, ANT+, NFS, or other communication technology configured to transmit data to and receive data from the edge computing device 200 and/or computer 300. In some configurations, the network interface 40 may be configured to communicate directly with a healthcare provider, emergency dispatch system, or third party. The network interface 40 may be configured to receive, process, and store data received from the health monitor and/or edge computing device 200. The network interface 40 may comprise a communication platform configured to user internet connection technology such as TCP/IP to send, receive, and share information such as a user's biographic information or sensor module data.

The edge computing device 200 may comprise edge hardware 210. The computer may comprise computer hardware 310. The edge hardware 210 and the computer hardware 310 may comprise a processor, memory, tangible computer readable storage media, a network interface, ports, motherboards, system buses, and other computer-related hardware adapted to allow the edge computing device and/or computer run the health application. The edge computing device 200 and computer 300 may also comprise a housing 90, an operating system 220, and software applications 225.

Figure 3:
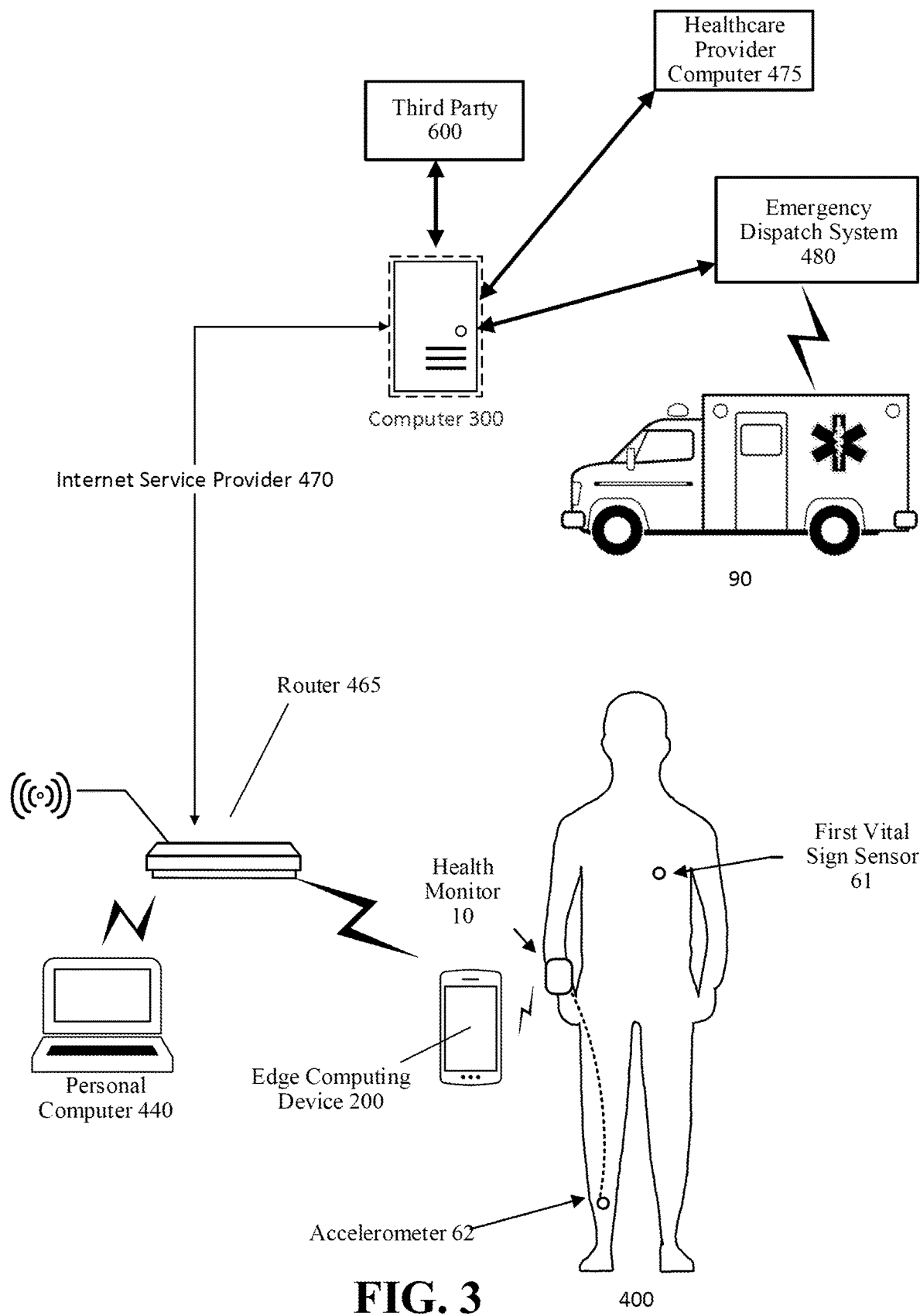
FIG. 3 depicts an alternate view of the monitoring system.

FIG. 3 shows a schematic diagram of the health monitor 10, edge computing device 200, and computer 300. The user 400 is shown wearing a heart rate sensor 61 and an accelerometer sensor 62 on his ankle, but the user could be wearing additional sensors. The health monitor 10 may also comprise additional sensors inside of the housing of the health monitor. The health monitor 10 may use its network interface to communicate with the edge computing device. The edge computing device may communicate via wifi to a router 465. The router 465 may send and receive transmissions to the computer 300. The computer 300 may be remotely or locally located. Lightning bolts are shown in FIG. 3 to illustrate a wireless communication protocol such as Bluetooth or ANT+ between the edge computing device and the health monitor 10. The edge computing device 200 and computer 300 may use a wireless network to communicate—the wireless network could be generated by a router 465. The configuration of FIG. 3 shows a personal computer 440 as an additional computing device. The personal computer 440 may also be in communication with the edge computing device 200 via the router 465. Control of communications between the health monitor 10 and/or edge computing device 200 may go through the personal computer 440. In other configurations, the health monitor 10 and/or edge computing device 200 may communicate with the computer 300. An internet service provider 470 may be configured to provide internet-based communications between the router 465 and the computer 300.

Computer 300 may be a server configured to communicate with a healthcare provider computer 475, third party 600, and/or a health dispatch system 480. In some configurations, the healthcare provider computer 475, third party 600, and health dispatch system 480 are computers themselves. For example, the computer 300 could alert a doctor of the user of the health monitor 10 of a change in heart rate rhythm (through an EKG sensor), by sending a communication to the healthcare provider computer 475. A healthcare provider computer 475 could be a terminal, a remote health care system (like a software as service patient management system), or even a smartphone of the doctor, nurse, or receptionist. The health dispatch system 480 could be a smartphone of an emergency contact of the user of the health monitor 10. It also could be a computer and related software operated by an emergency response team at a hospital. It may also be a computer system operated by a service provider configured to contact a hospital or paramedic team if it receives a communication from the computer 300, edge computing device 200, or health monitor 10 indicating that the user required medical or technical assistance.

The health monitor 10 may comprise a memory 30 configured to store a health application 36. The edge computing device may also comprise a health application 36. The health application 36 may control a data access module 32, data storage logic 34, and an alarm trigger 500.

Figure 4:
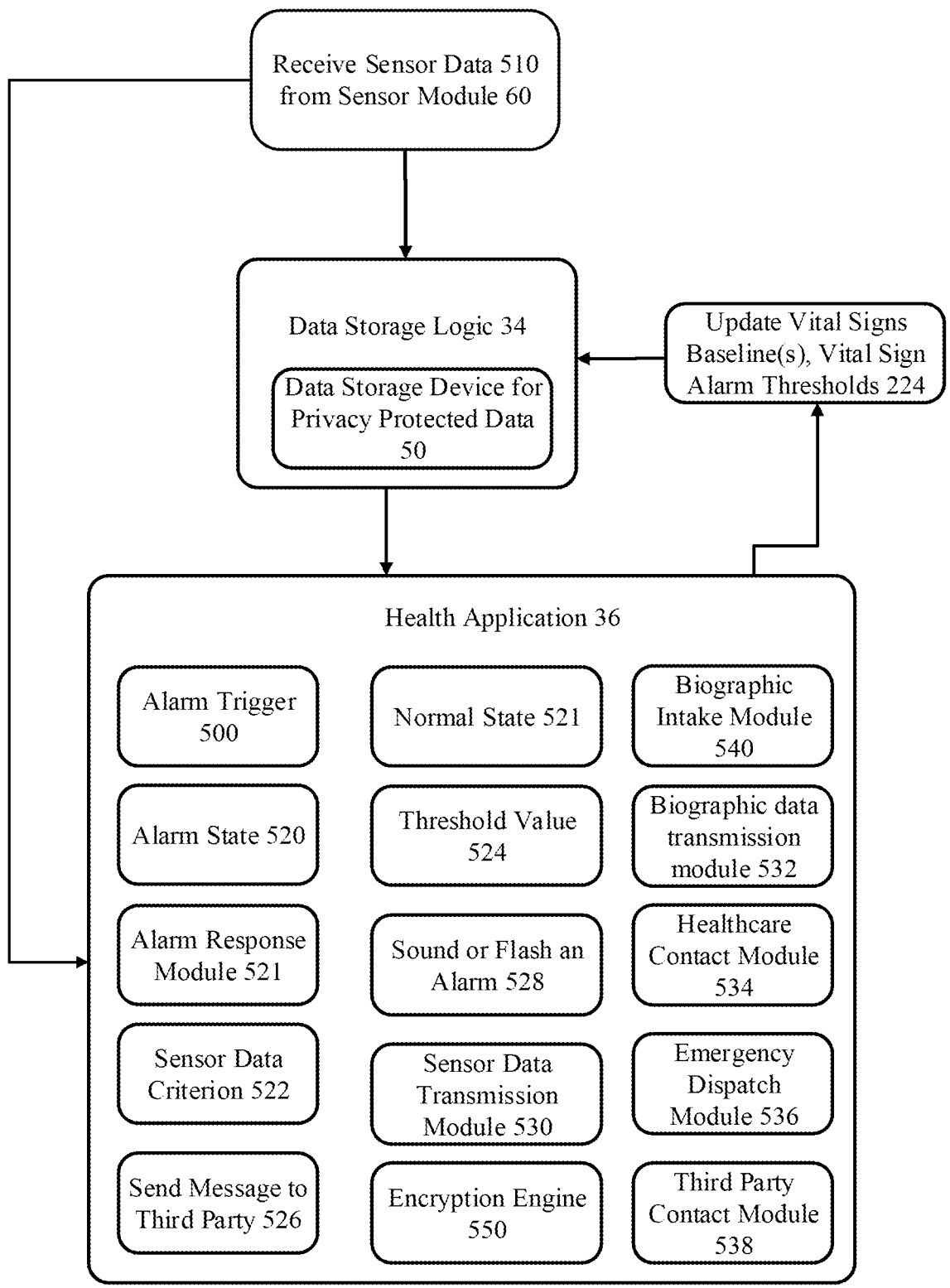
FIG. 4 illustrates a view of the health application.

FIG. 4 illustrates some exemplary process flow and certain functions of the health application 36. Step 510 shows receiving sensor data from the sensor module. As previously described, the sensor data could be vital signs, ambient conditions, position information, etc. The data storage logic 34 may be configured to store the data from the sensor module 60 into the data storage device 50 for privacy protected data. The data storage device may be located in the health monitor, the edge computing device, or the computer. Some configurations may feature two or three data storage devices in one or more of the health monitor 10, the edge computing device 200, or the computer 300.

The health application 36 may comprise an alarm trigger 500 which may be configured to trigger an alarm if sensor data does not meet a predetermined criterion (e.g. goes above or below a preset threshold). The alarm trigger 500 may be configured to receive sensor data from the sensor module directly. Or, the alarm trigger may access data stored in the data storage device 50. The health monitor, edge computing device, and/or computer may comprise an alarm trigger. Some configurations may feature two or three alarm triggers in one or more of the health monitors, the edge computing devices, or the computers.

The alarm trigger may have an alarm state 520 and a normal state 521. Whether the alarm trigger is in an alarm state or a normal state may depend on whether the received sensor meets or does meet not a criterion. A criterion could require, for example, that a first sensor value is below a first threshold, a second sensor value is above a second threshold, a third sensor value is not above a third threshold, a fourth sensor value is below a fifth threshold and above a sixth threshold, or a fifth sensor value is above a seventh threshold or below an eighth threshold. The alarm trigger could be configured to switch to an alarm state if any of the sensor values do not meet a predetermined criterion, all of the sensor values do not meet a predetermined criterion, or a portion of the sensor values do not meet a predetermined criterion. Examples of sensor values are explained above, but they may include values like heart rate, external temperature, humidity, and acceleration. A criterion may not be met if a sensor data value falls below a threshold. Or a criterion may be met if a sensor data value is maintained between two thresholds. A criterion may be a value set by user to cause the alarm trigger and/or health application to take an action if the health application receives data from the sensor module that is above or below the criterion. A criterion may be a value determined by an industry standard, medical research, or physiological based formula. For example, medical research may indicate that a blood oxygen percentage under 84% is unsafe. The health monitor may comprise a criterion preset such that it will enter an alarm state if the blood oxygen percentage falls below the criterion (84% in this example.) The threshold may be a range or it may include an average value over a function of time. The alarm trigger may be configured so that it does not enter an alarm state if sensor data is maintained with a range, above a certain value, or below a certain value. For example, the alarm trigger could be configured so that it does not enter an alarm state as long the user's average heart rate per minute is 180 beats per minute or 900 beats in five minutes.

Additionally, the alarm trigger may enter the alarm state if no data is being received from the sensor module or if the data has been corrupted.

A user of the health monitor 10 may configure the health monitor and/or edge computing device to transmit none, some, or all of the sensor module data to computer 300 using the command module 80. This transmission of sensor module data may be conditioned upon the sensor module meeting or not meeting a criterion. In some cases, transmission of the sensor module data may require an approval from the user (see FIG. 10, element 1000). In some configurations (see FIG. 8 for example), the health monitor 10 may comprise an alarm response module 651 configured to receive sensor module criterion settings 640 and an alarm trigger action(s) 650. The command module 80 may request the user to designate actions for the health monitor, edge computing device, or computer to take if sensor module data does not meet a criterion.

When the alarm trigger enters an alarm state, the alarm trigger may be configured to take an action. Actions may be selected by the user and there may be default actions preset in the health application. Examples of actions may include sounding an audible alarm or flashing a visual alarm, electronically notifying a third party (texting, calling, emailing the third party, etc.), or electronically notifying the computer 300. The electronic notification could simply include a message that alarm trigger is in an alarmed state. Additionally, the notification could include biographic information about the user such as a userID, name, address, phone, DOB, medical history, email, etc. The biographic information could be stored directly in the data storage device 50 or it could be linked in a database managed by the computer. The user could save his or her biographic information into the computer via an online access interface during an account creation process. The user may save his or her biographic information into the health monitor or edge computing device through the command module. The biographic information may be preexisting in the health monitor, edge computing device, or computer. For example, a user might enter certain biographic information into the operating system of the edge computing device. The health application may be configured to access this biographic information. The Apple Health App which makes health related information about a user accessible to multiple application is an example.

The third party that might be notified by the health application 36 via the third party contact module 538 could be an emergency point of contact, a person determined by the health app to be in close proximity, a healthcare provider, attorney, friend, neighbor, manager, paramedic, emergency dispatch operator, doctor, family person, or another individual or entity selected by the user of the health application.

The health application 36 may be configured to have third party contact information set by default. For example, the health application may be preconfigured to call 911 if the body temperature of the user exceeds 104 degrees Fahrenheit for than 10 minutes.

The health application 36 may determine a second health monitor is nearby a first health monitor in several ways. In some configurations, the computer may have access to a plurality of health monitors. As part of the data transmitted to the computer by the health monitor, the computer may receive sensor module data containing GPS or location data of the health monitor. The computer may comprise a proximity module to determine a nearby or closest second monitor to a first monitor. In some configurations, the health monitor or the edge computing device may be configured to detect whether a second edge computing device or second health monitor is in network range. For example, the first health monitor may be configured to determine if a second health monitor is emitting a Bluetooth signal. The Bluetooth signal could comprise an identifier of the second health monitor. The first health monitor may be connected to a router having a wireless network. The first health monitor may be configured to determine whether there is a second health monitor connected to the same router.

A second health monitor may be considered to be nearby a first health monitor if the health application determines both monitors are connected to a network having a limited range (such as ANT+, WIFI, Bluetooth, etc.) In other cases, the health application can determine a second health monitor is nearby a first monitor by determining a distance between two devices is less than a physical distance threshold. For example, two health monitors may be nearby each other if the physical distance separating them is less 1000 feet. The health application may consider population density when setting the physical distance threshold. For example, in an urban area the physical distance threshold may be less than a physical distance threshold for a rural area.

The data access module 32 (see FIG. 2) may require the user or third party attempting to access the data present a credential to access the data. The data access module may control whether an individual can use the health application. A credential could be a passcode, password, gesture, fingerprint, etc.

The user may be able to select whether the health monitor is configured to send or not send sensor information to the edge computing device when the alarm trigger is in the normal state. In some configurations, the health application of the health monitor is configured to send sensor module data to the edge computing device at a predetermined interval (e.g. every 5 seconds.) The edge computing device 200 may analyze the sensor module data, determine it does not meet a criterion, and send an alert to the computer including some biographic information of the user and the sensor module data. The computer may contact a third party to alert the third party that the sensor module data of the user does not meet a criterion. The computer may provide the third party with the user's location data or home address. The health application and/or alarm trigger may comprise a sensor data transmission module 530 for transmitting data from the sensor module to a third party or computer, biographic data transmission module 532 for transmitting data to the computer, a healthcare contact module for contacting a healthcare provider 476, an emergency response dispatch module 536 for contacting an emergency response dispatch module 536, and a third-party contact module 538 for contacting a third party 600.

The health monitor 10 and/or the edge computing device 200 may be configured to request the user approve transmission (e.g. the third party contact module may require the user enter an approval message) of his or her sensor module data and/or biographic information to the computer or third party before the health monitor or edge computing device can send the sensor module data and/or biographic information. In some cases, only the sensor module data that does not meet the criterion may be sent to the computer or third party. In other cases, all of the sensor module data may be transmitted to the computer or third party. The health monitor and/or the edge computing device may be configured to automatically transmit sensor module data and/or biographic information of the user to the computer or third party if the sensor module data does not meet a criterion.

The health application of the health monitor and/or edge computing device may generate a message to a third party or the computer. This message may be encrypted with an encryption engine 550 so that only an authorized third party or authorized computer can decrypt the message. The encryption engine 550 may also encrypt or secure sensor module data. In some configurations, the data storage logic 34 may invoke the encryption engine 550 to encrypt the received sensor module data. The health application may use known encryption techniques such a public and private keys to protect the sensor data and biographic data from access by authorized parties. In some configurations, the data storage logic may have its own encryption routines or not use encryption at all when storing data. The data storage logic may use other known techniques other than encryption for securing sensor module data from unauthorized access.

Figure 5:
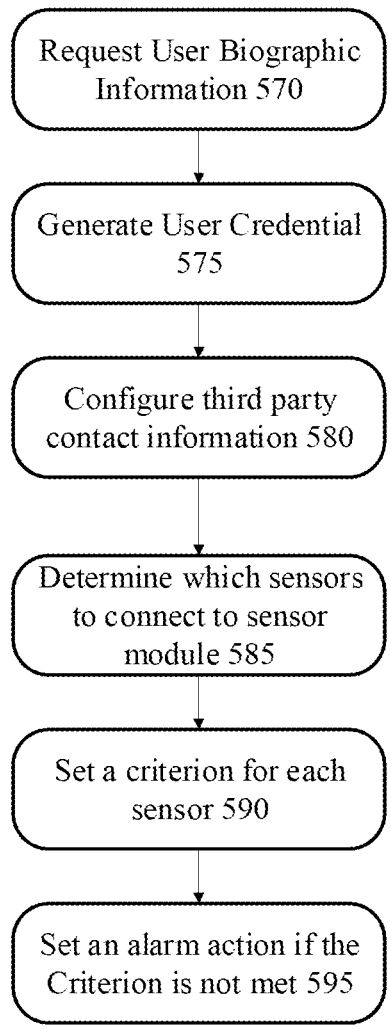
FIG. 5 illustrates a flow chart of a setup routine for the health monitor.

FIG. 5 shows an exemplary setup method for the health application. The setup method may comprise requesting user biographic information 570, generating a user credential 575, configuring third party contact information 580, determining which sensors to connect to the sensor module 585, setting a criterion one or more sensors 590, and setting an alarm action if the criterion is not met 595. In some configurations, the method may not include setting a criterion for one or more sensors. In such a configuration, the health monitor may display the sensor data (e.g. heart rate) on a display or the edge computing device may display the sensor data on a display. The health application may be configured to display and/or record the sensor data even if no criterion is set.

Figure 6:
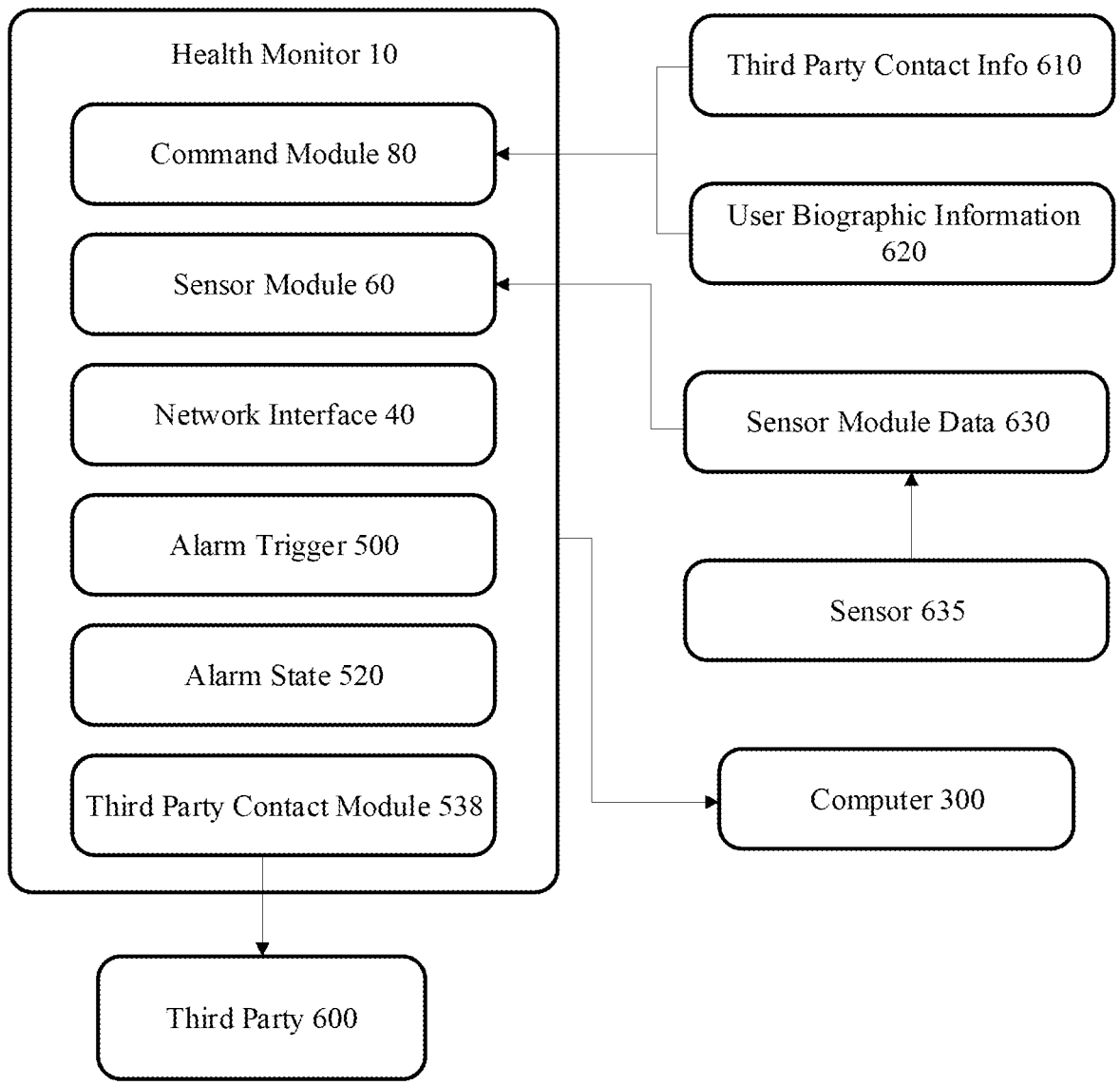
FIG. 6 illustrates a process flow for monitoring the health of a user.

FIG. 6 illustrates a health monitor 10 comprising a third-party contact module 538 configured to transmit third party contact information to a third party 600. The user may provide third-party contact information 610 to the health monitor via the command module 80. The user may provide biographic information 620 about himself or herself to the health monitor 10 using the command module 80. The health monitor 10 may contain a health application 36 comprising an alarm trigger 500 configured to transmit third-party contact information 610, biographic information 620, and sensor module data 630 from a sensor 635 to the computer 300 if the alarm trigger enters an alarm state. The health monitor 10 may be connected to the computer using a network interface. The computer 300 or health monitor 10 may comprise a third-party contact module 538 configured to send a message to a third party. The message (900, FIG. 9) may comprise sensor module data 630 and the biographic information 620 of the user. The health monitor 10 may be configured to transmit the biographic information 620 and/or sensor module data 630 to the third party 600 if the alarm trigger enters an alarm state 520. Additionally, the health monitor 10 may comprise an emergency dispatch module 536 and/or healthcare contact module 534 for contacting an emergency dispatch system 480 and/or healthcare provider computer 475 respectively.

In other configurations, the health application 36 of the edge computing device 200 may comprise the third-party contact module 538 to send a message to a third party 600. The edge computer device 200 may be configured to transmit the biographic information 620 and/or sensor module data 630 to the third party 600 if the alarm trigger 500 enters an alarm state 520. Additionally, the edge computing device 200 may comprise an emergency dispatch module 536 and/or healthcare contact module 534 for contacting an emergency dispatch system 480 and/or healthcare provider computer 475 respectively.

Figure 7:
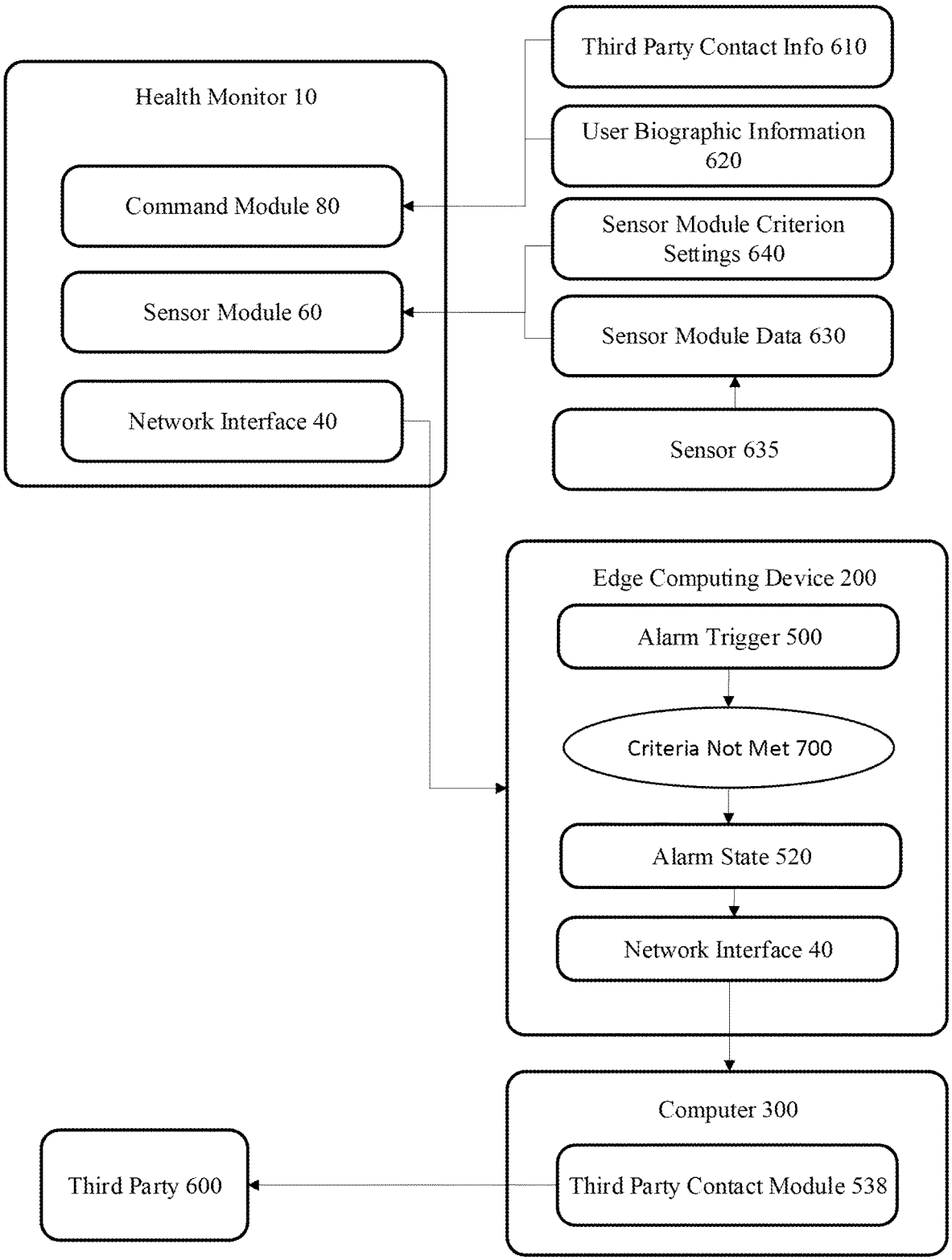
FIG. 7 illustrates a second process flow for monitoring the health of a user.

FIG. 7 depicts a health monitor comprising a command module 80, sensor module 60, and network interface 40. The command module 80 may be configured to receive third-party contact information 610 and user biographic information 620. The sensor module 60 may be configured to receive sensor module data 630 from one or more sensors 635. The sensor module 60 may be configured to receive a sensor module criterion 640. The sensor module criterion may be setting or a level. Multiple sensor module criteria may also be provided to the sensor module 60. The health monitor 10 may be configured to connect an edge computing device 200 with a network interface 40. The edge computing device 200 may comprise an alarm trigger 500 configured to enter into an alarm state 520 if the sensor module data 630 does not meet a criterion 700. A network interface 40 may be configured to transmit the third-party contact information, user biographic information, and sensor module data to the computer 300 if the criterion is not met. The computer may contact a third party 600 via a third-party contact module 538 to alert the third-party certain sensor module data of the user (as specified by the user biographic data) does not meet a sensor module criterion 640 set by the user.

For example, the system of FIG. 7 may have a health monitor connected to an EKG sensor. The EKG sensor may be configured to measure hearth rhythm of a user. The network interface of the health monitor may be configured to transmit EKG sensor data to the edge computing device. The edge computing device 200 may comprise an alarm trigger 500 configured to transmit a message to the computer. The alarm trigger may be configured to enter an alarm state if the EKG sensor data does not meet a criterion. The computer may comprise a healthcare contact module 534 configured to contact a healthcare provider 476 if the alarm trigger 500 has entered the alarm state 520.

Figure 8:
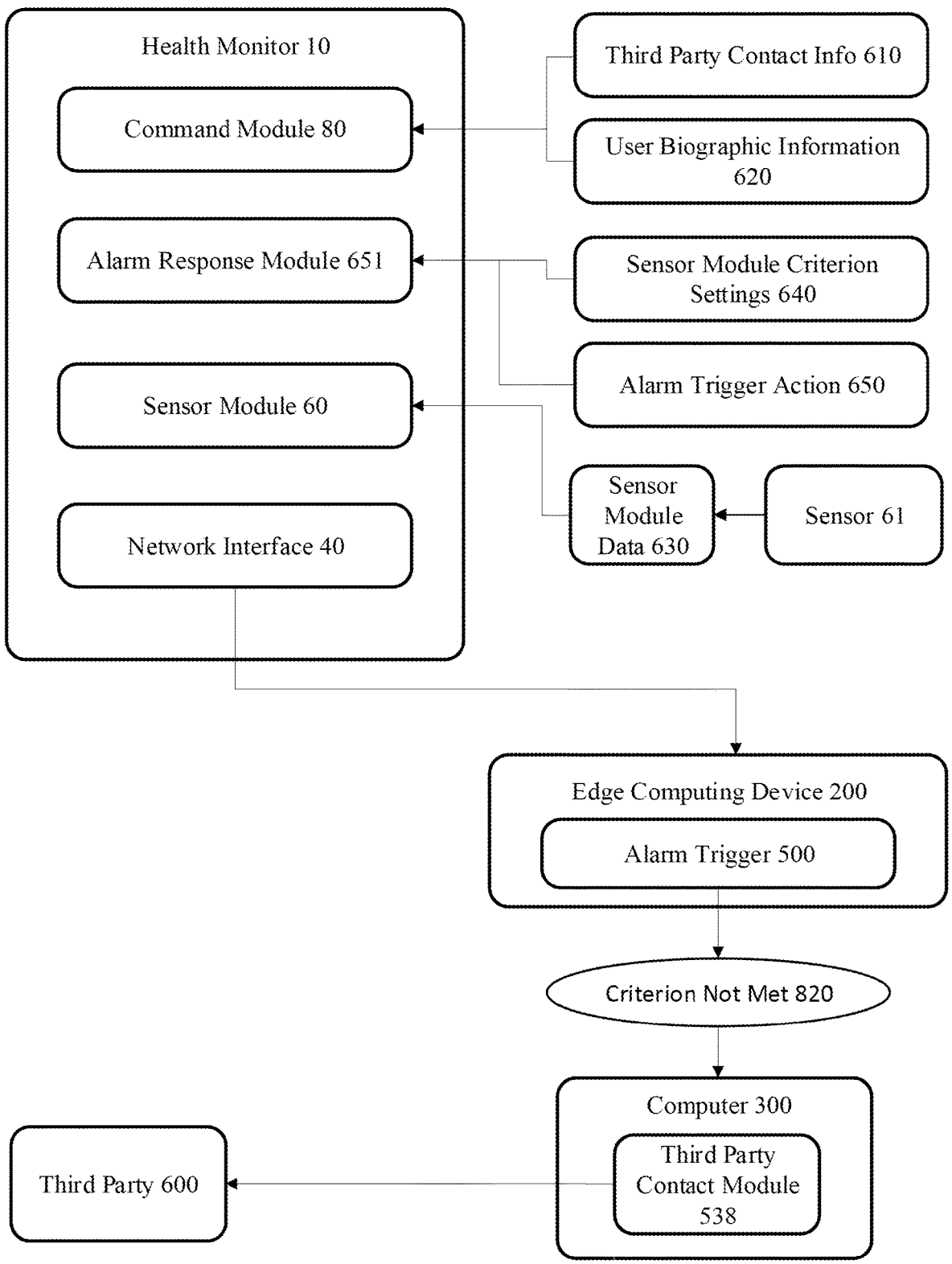
FIG. 8 illustrates a third process flow for monitoring the health of a user.

FIG. 8 shows a schematic view of the system comprising a health monitor 10, edge computing device 200 and computer 300. The health monitor 10 may comprise a command module 80 configured to display a prompt to a user requesting the user provide information to the data storage device 50 of the health monitor 10. For example, the display may prompt the user to enter third party contact information 610, user biographic information 620, sensor module data 630, sensor module criterion settings 640, and an alarm trigger action 650. The third-party contact information 610 may include name, address, email, location, phone, work address, IP address, MAC Address, Network address or other information relevant for contacting a third party. The user biographic information 620 may contain information about the user of health monitor such as name, address, email, location, phone, work address, IP address, MAC Address, Network address or other information relevant for contacting the user. The command module 80 or the alarm response module 651 may receive an alarm trigger action 650 and sensor module data 630. An alarm trigger action 650 may be an action for the health monitor 10, edge computing device 200, and/or computer 300 to take if the sensor module data does not meet sensor module criterion. For example, the alarm trigger action 650 could instruct the health monitor to flash an alarm or to instruct the edge computing device to call 911 (using, for example, an emergency dispatch module 536, FIG. 4.) Sensor module data 630 may include data from one or more sensors 61 as described above. The health monitor 10 may comprise a network interface 40 for communication with one or more other devices such as the edge computing device 200, computer 300, or a second health monitor 11, FIG. 9.

FIG. 8 shows that the health monitor 10 is in communication with an edge computing device 200. The edge computing device 200 is communication with a computer. The computer 300 is communication with a third party 600. Alternative configurations are possible . . . such as the health monitor may be in direct communication with the computer 300 or third party 600. As shown, the alarm trigger 500 of the edge computing device 200 may enter an alarm state 520 and send a message to the computer 300 if the sensor module data 630 does not meet the sensor module criterion 820. The third-party contact module 538 may send the message to the third party 600.

Figure 9:
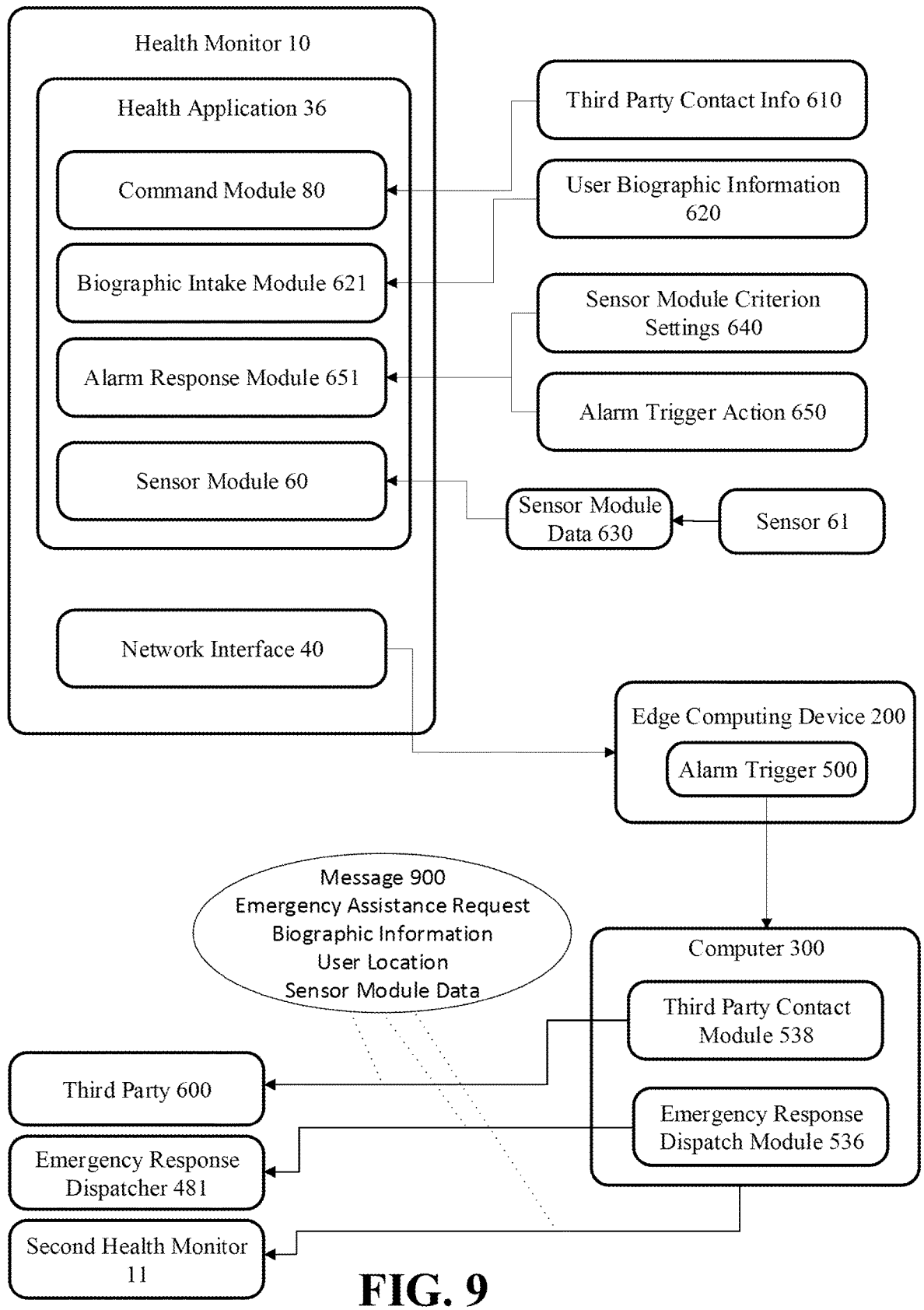
FIG. 9 illustrates a fourth process flow for monitoring the health of a user.

FIG. 9 shows a system comprising a health monitor 10, edge computing device 200, and computer 300. Many elements from FIG. 8 also appear in FIG. 9, and their function and structure may be the same or similar. In FIG. 9, a biographic intake module 621 is configured to receive user biographic information 620. One or more of the modules (command module 80, biographic intake module 621, alarm response module 651 sensor module 60) may be controlled by or be a component of the health application 36 running on the health monitor 10. The biographic intake module 621 may comprise similar structure as the command module 80, be connected to the command module 80, or be a component of the command module. In FIG. 9, the computer 300 is shown to comprise an emergency response dispatch module 536. The emergency response dispatch module 536 may be configured to contact an emergency response dispatcher 481. An emergency response dispatcher 481 could be a hospital, firefighter, police, military, etc. The computer 300 may also be connected to a second health monitor 11. The computer may transmit a message 900 to the third party 600, emergency response dispatcher 481, and second health monitor 11. The message 900 may include information such an emergency assistance request, biographic, user location, and/or sensor information. The source of this information may originally come from the command module 80 and/or the sensor module 60.

Figure 10:
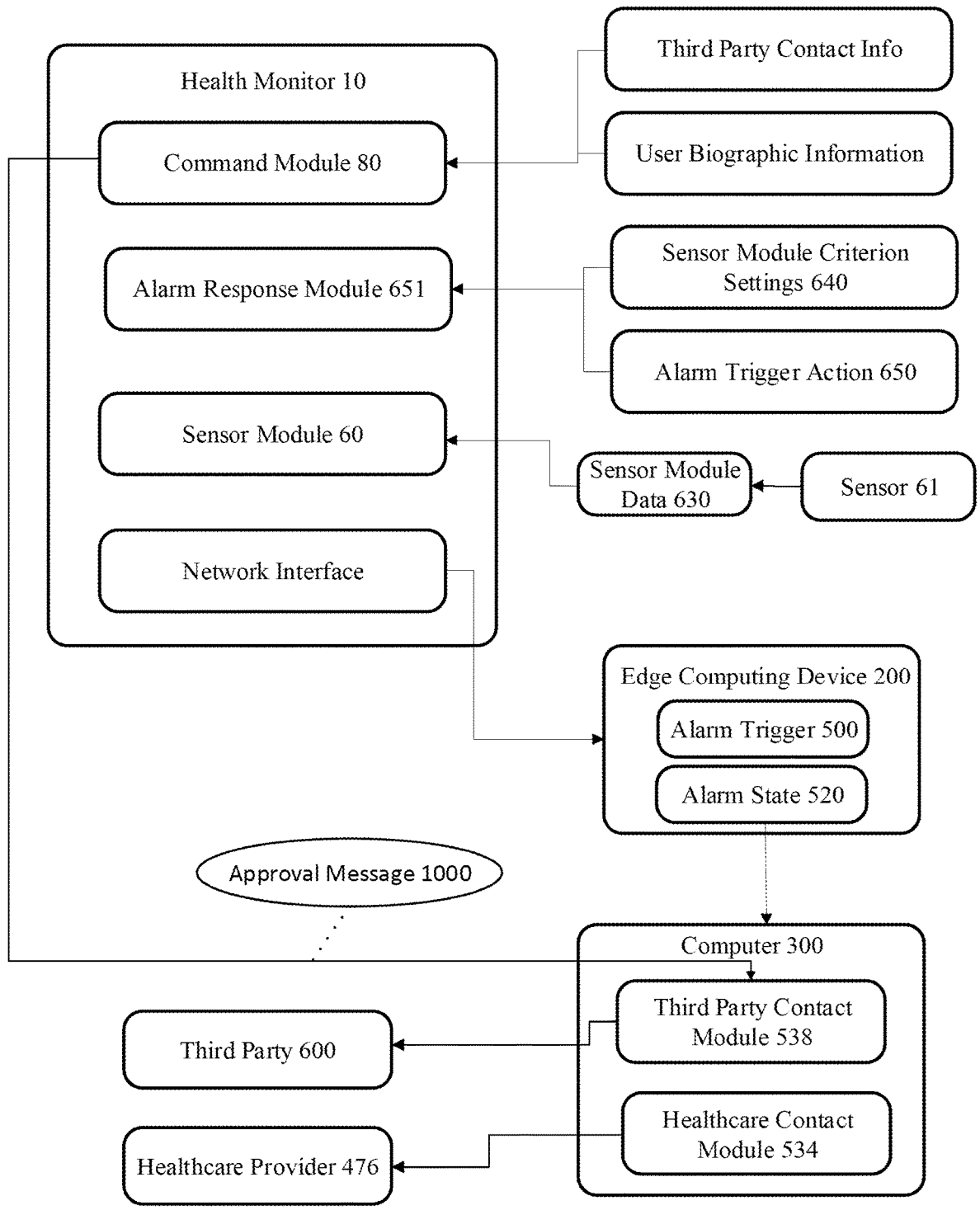
FIG. 10 illustrates a fifth process flow for monitoring the health of a user.

FIG. 10 shows a system comprising a health monitor 10, edge computing device 200, and computer 300. Many elements from FIG. 9 also appear in FIG. 10, and their function and structure may be similar. In FIG. 10, the edge computing device 200 may comprise an alarm trigger 500 having an alarm state 520. The computer 300 may be configured to contact a third party 600 with a message as explained in reference to FIG. 9. Similarly, the computer 300 may be comprise a health contact module 534 configured to send the message 900 to healthcare provider 476. The computer 300 may be configured to require the health monitor 10 (or user) to submit an approval message 1000 before the computer 300 can send the message to a third party or healthcare provider 476. In other configurations, the edge computing device 200 may be configured to require an approval message 1000 from the health monitor 10 or user

400. In other configurations, the computer 300 may require the edge computing device 200 provide an approval message 1000.

Figure 11:
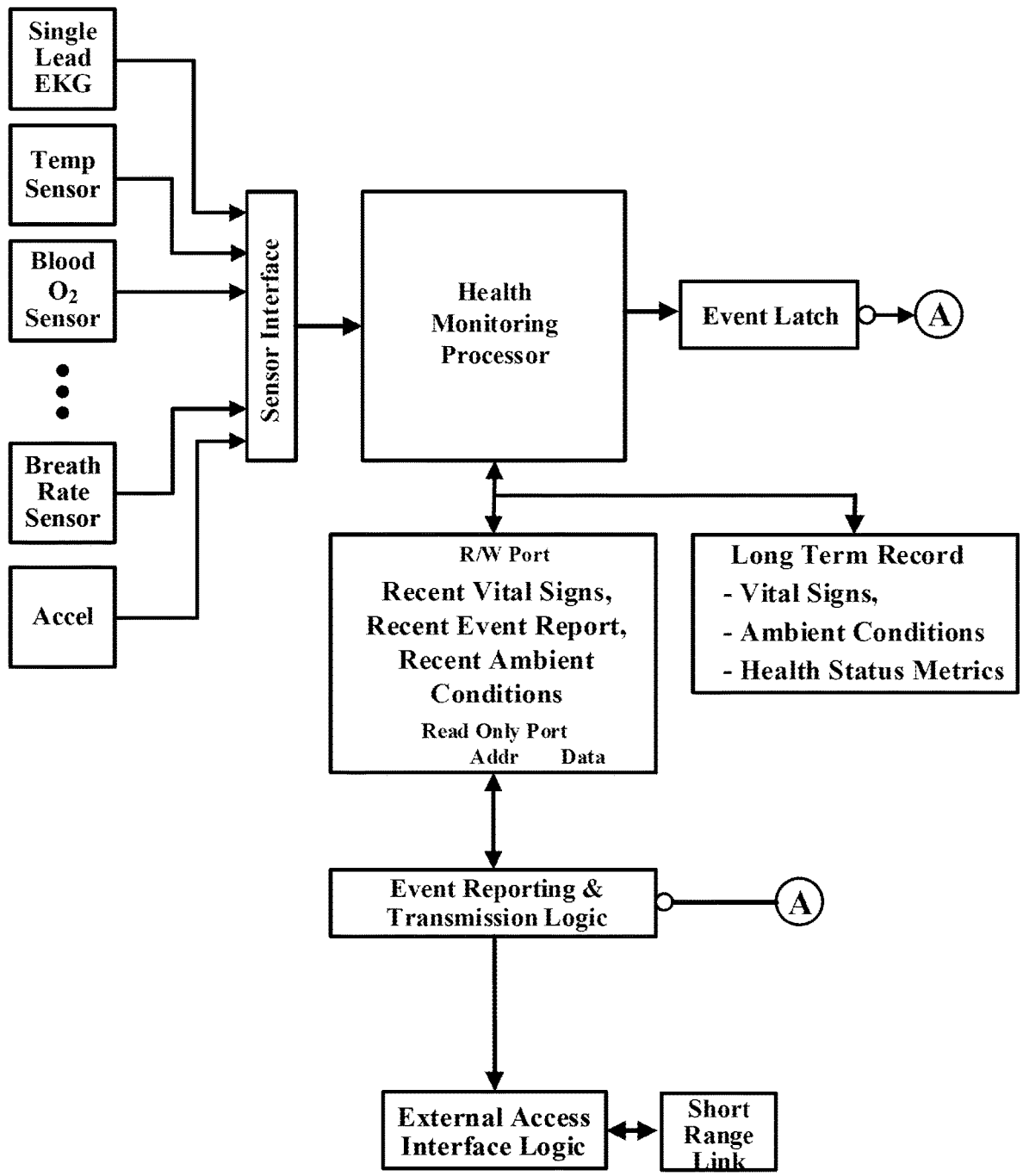
FIG. 11 illustrate a schematic diagram of the system for monitoring the health of a user.

FIG. 11 illustrates a functional block schematic of a privacy protective wearable health monitor device, for systems and methods of privacy protective wearable, edge computing supported monitoring and reporting of health condition in accordance with various embodiments.

Figure 12:
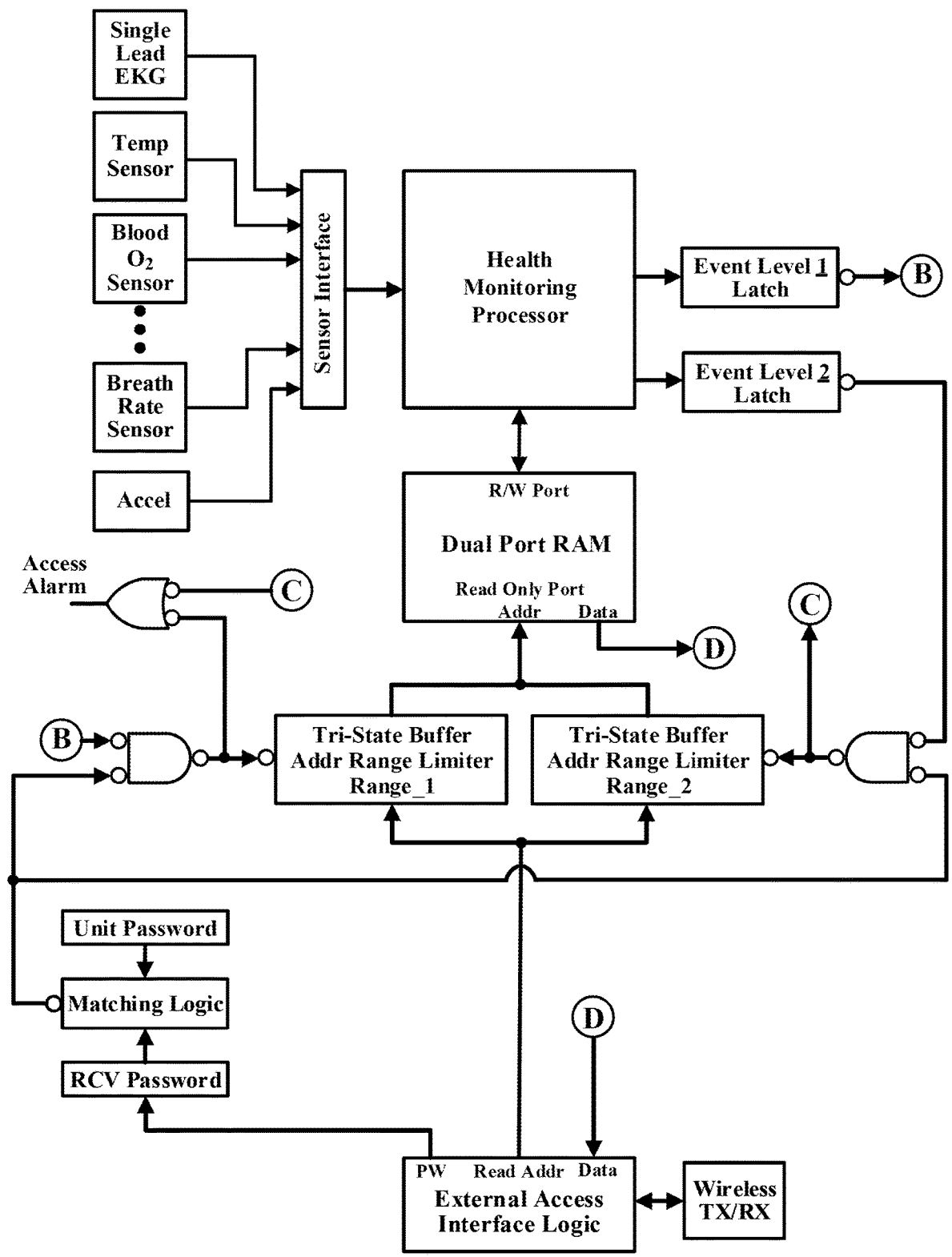
FIG. 12 illustrates a second schematic diagram of the system for monitoring the health of a user.

FIG. 12 illustrates a functional block schematic of another privacy protective wearable health monitor device, for systems and methods of privacy protective wearable, edge computing supported monitoring and reporting of health condition in accordance with various embodiments.

Figure 13:
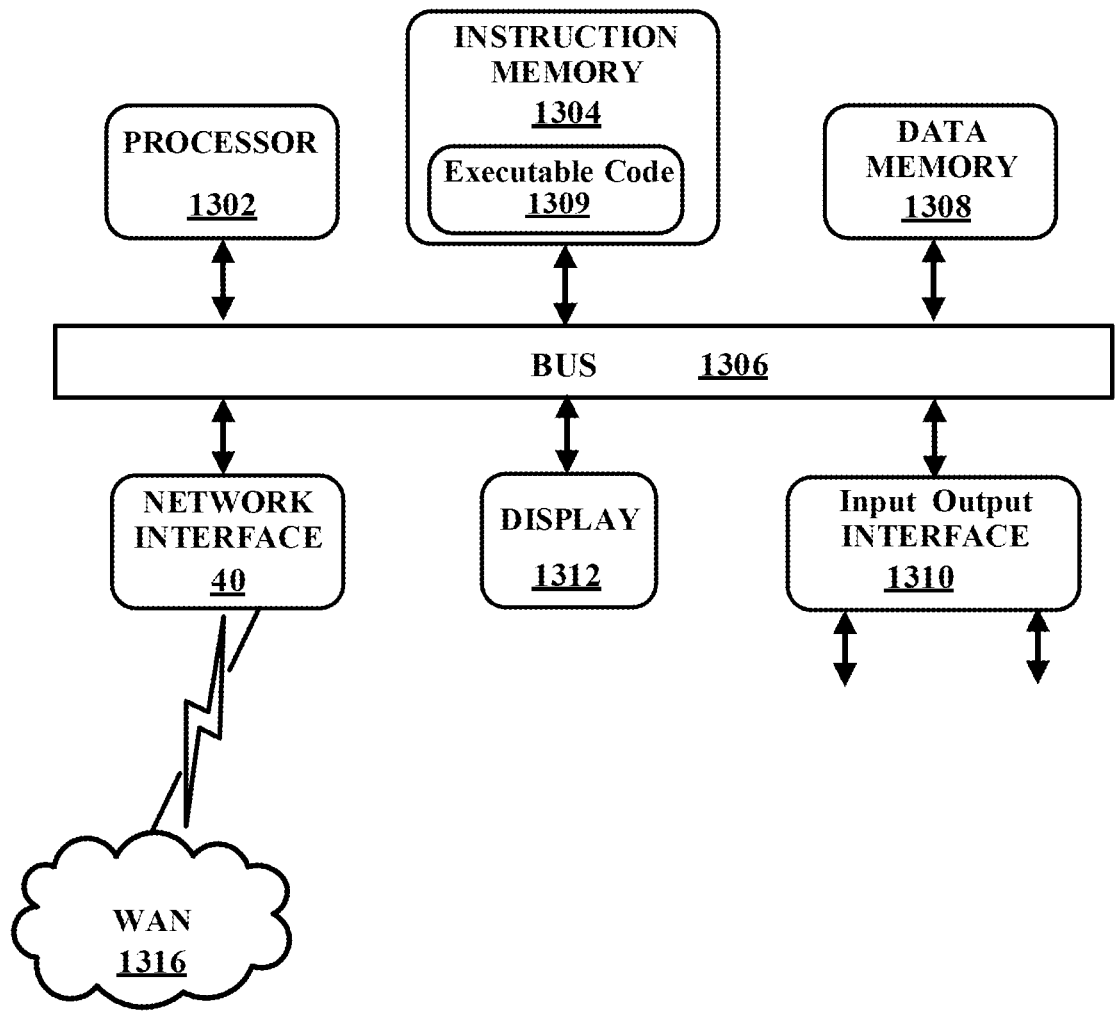
FIG. 13 illustrates a computing system on which aspects of the present disclosure can be practiced.

FIG. 13 illustrates, in simplified schematic form, a computer system on which aspects of the present disclosure can be practiced. The computer system can include a hardware processor 1302 communicatively coupled to an instruction memory 1304 and to a data memory 1308. The instruction memory 1304 can be configured to store, on at least a non-transitory computer readable medium as described in greater detail below, executable program code. The hardware processor 1302 may include multiple hardware processors and/or multiple processor cores. The hardware processor 1302 may include hardware processors from different devices, which cooperate. The computer system may execute one or more basic instructions included in the memory executable program code in instruction memory 1304.

The computer system may comprise a bus 1306 having input output interface 1310. The computer system may comprise a display 1312 and a network interface 40. The computer and network interface may be connected to another computer system via a wide area network 1316.

Relationship Between Hardware Processor and Executable Program Code

A hardware processor 1302 may be thought of as a complex electrical circuit that is configured to perform a predefined set of basic operations in response to receiving a corresponding basic instruction selected from a predefined native instruction set of codes.

The predefined native instruction set of codes is specific to the hardware processor; the design of the processor defines the collection of basic instructions to which the processor will respond, and this collection forms the predefined native instruction set of codes.

A basic instruction may be represented numerically as a series of binary values, in which case it may be referred to as a machine code. The series of binary values may be represented electrically, as inputs to the hardware processor, via electrical connections, using voltages that represent either a binary zero or a binary one. These voltages are interpreted as such by the hardware processor.

Executable program code may therefore be understood to be a set of machine codes selected from the predefined native instruction set of codes. A given set of machine codes may be understood, generally, to constitute a module. A set of one or more modules may be understood to constitute an application program or "app." An app may interact with the hardware processor directly or indirectly via an operating system. An app may be part of an operating system.

Computer Program Product

A computer program product is an article of manufacture that has a computer-readable medium with executable program code that is adapted to enable a processing system to perform various operations and actions.

A computer-readable medium may be transitory or non-transitory.

A transitory computer-readable medium may be thought of as a conduit by which executable program code may be provided to a computer system, a short-term storage that may not use the data it holds other than to pass it on.

The buffers of transmitters and receivers that briefly store only portions of executable program code when being downloaded over the Internet is one example of a transitory computer-readable medium. A carrier signal or radio frequency signal, in transit, that conveys portions of executable program code over the air or through cabling such as fiber-optic cabling provides another example of a transitory computer-readable medium. Transitory computer-readable media convey parts of executable program code on the move, typically holding it long enough to just pass it on.

Non-transitory computer-readable media may be understood as a storage for the executable program code. Whereas a transitory computer-readable medium holds executable program code on the move, a non-transitory computer-readable medium is meant to hold executable program code at rest. Non-transitory computer-readable media may hold the software in its entirety, and for longer duration, compared to transitory computer-readable media that holds only a portion of the software and for a relatively short time. The term, "non-transitory computer-readable medium," specifically excludes communication signals such as radio frequency signals in transit.

The following forms of storage exemplify non-transitory computer-readable media: removable storage such as a universal serial bus (USB) disk, a USB stick, a flash disk, a flash drive, a thumb drive, an external solid-state storage device (SSD), a compact flash card, a secure digital (SD) card, a diskette, a tape, a compact disc, an optical disc; secondary storage such as an internal hard drive, an internal SSD, internal flash memory, internal non-volatile memory, internal dynamic random-access memory (DRAM), read-only memory (ROM), random-access memory (RAM), and the like; and the primary storage of a computer system.

Different terms may be used to express the relationship between executable program code and non-transitory computer-readable media. Executable program code may be written on a disc, embodied in an application-specific integrated circuit, stored in a memory chip, or loaded in a cache memory, for example. Herein, the executable program code may be said, generally, to be "in" or "on" a computer-readable media. Conversely, the computer-readable media may be said to store, to include, to hold, or to have the executable program code.

Creation of Executable Program Code

Software source code may be understood to be a human-readable, high-level representation of logical operations. Statements written in the C programming language provide an example of software source code.

Software source code, while sometimes colloquially described as a program or as code, is different from executable program code. Software source code may be processed, through compilation for example, to yield executable program code. The process that yields the executable program code varies with the hardware processor; software source code meant to yield executable program code to run on one hardware processor made by one manufacturer, for example, will be processed differently than for another hardware processor made by another manufacturer.

The process of transforming software source code into executable program code is known to those familiar with this technical field as compilation or interpretation and is not the subject of this application.

User Interface

A computer system may include a user interface controller under control of the processing system that displays a user interface in accordance with a user interface module, i.e., a set of machine codes stored in the memory and selected from the predefined native instruction set of codes of the hardware processor, adapted to operate with the user interface controller to implement a user interface on a display device. Examples of a display device include a television, a projector, a computer display, a laptop display, a tablet display, a smartphone display, a smart television display, or the like.

The user interface may facilitate the collection of inputs from a user. The user interface may be graphical user interface with one or more user interface objects such as display objects and user activatable objects. The user interface may also have a touch interface that detects input when a user touches a display device.

A display object of a user interface may display information to the user. A user activatable object may allow the user to take some action. A display object and a user activatable object may be separate, collocated, overlapping, or nested one within another. Examples of display objects include lines, borders, text, images, or the like. Examples of user activatable objects include menus, buttons, toolbars, input boxes, widgets, and the like.

Communications

The various networks are illustrated throughout the drawings and described in other locations throughout this disclosure, can comprise any suitable type of network such as the Internet or a wide variety of other types of networks and combinations thereof. For example, the network may include a wide area network (WAN), a local area network (LAN), a wireless network, an intranet, the Internet, a combination thereof, and so on. Further, although a single network is shown, a network can be configured to include multiple networks.

CONCLUSION

For any computer-implemented embodiment, "means plus function" elements will use the term "means;" the terms "logic" and "module" have the meaning ascribed to them above and are not to be construed as generic means. An interpretation under 35 U.S.C. § 112(f) is desired only where this description and/or the claims use specific terminology historically recognized to invoke the benefit of interpretation, such as "means," and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features or methodological steps, it is to be understood that the subject matter defined in the appended claims is not necessarily limited to the specific features or steps described. Rather, the specific features and steps are disclosed as example forms of implementing the claimed subject matter. To the extent headings are used, they are provided for the convenience of the reader and are not be taken as limiting or restricting the systems, techniques, approaches, methods, or devices to those appearing in any section. Rather, the teachings and disclosures herein can be combined or rearranged with other portions of this disclosure and the knowledge of one of ordinary skill in the art. It is intended that this disclosure encompass and include such variation. The indication of any elements or steps as "optional" does not indicate that all other or any other elements or steps are mandatory. The claims define the invention and form part of the specification. Limitations from the written description are not to be read into the claims.

Certain attributes, functions, steps of methods, or sub-steps of methods described herein may be associated with physical structures or components, such as a module of a physical device that, in implementations in accordance with this disclosure, make use of instructions (e.g., computer executable instructions) that may be embodied in hardware, such as an application specific integrated circuit, or that may cause a computer (e.g., a general-purpose computer) executing the instructions to have defined characteristics. There may be a combination of hardware and software such as processor implementing firmware, software, and so forth so as to function as a special purpose computer with the ascribed characteristics. For example, in embodiments a module may comprise a functional hardware unit (such as a self-contained hardware or software or a combination thereof) designed to interface the other components of a system such as through use of an application programming interface (API). In embodiments, a module is structured to perform a function or set of functions, such as in accordance with a described algorithm. This disclosure may use nomenclature that associates a component or module with a function, purpose, step, or sub-step to identify the corresponding structure which, in instances, includes hardware and/or software that function for a specific purpose. For any computer-implemented embodiment, "means plus function" elements will use the term "means;" the terms "logic" and "module" and the like have the meaning ascribed to them above, if any, and are not to be construed as means.

While certain implementations have been described, these implementations have been presented by way of example only and are not intended to limit the scope of this disclosure. The novel devices, systems and methods described herein may be embodied in a variety of other forms; furthermore, various omissions, substitutions, and changes in the form of the devices, systems and methods described herein may be made without departing from the spirit of this disclosure.

What is claimed:

1. A system for monitoring a user comprising:
   an edge computing device comprising an operating system, a first network interface, and a software application;
   a computer, independent from the edge computing device, comprising a second network interface configured to receive information from the edge computing device; and
   a health monitor, independent from the edge computing device and the computer, wherein the health monitor is a wearable computer configured to attach to a hand, finger, wrist, ankle, or ear of the user, comprising:
      a processor for executing computer readable instructions;
      a memory containing tangible non-transitory memory containing the computer readable instructions; said computer readable instructions configured to cause the processor to execute a health application;
      a third network interface configured to send and receive wireless transmissions with the computer and the edge computing device, and configured to contact a healthcare provider or health dispatch system without interfacing with the computer or the edge computing device when a criterion is not met; wherein the wireless transmissions are sent to the computer, edge computing device, or healthcare provider upon approval of the user only when the criterion is met wherein when the criterion is not met, the wireless transmissions are sent to the computer, edge computing device, or healthcare provider without the approval of the user;

a sensor module connected to one or more sensors for receiving sensor data, wherein the received sensor data comprises different vital data from the user, ambient data surrounding the user and position data of the user;

a data storage logic configured to electronically store the sensor data in a data storage device;

a first data access module configured to retrieve the information from the data storage device;

an alarm trigger configured to enter into an alarm state if the criterion is not met; wherein the criterion comprises a combination of several thresholds, about the different vital data, the ambient data and the position data, that needs to be accomplished in order to determine that the criterion was not met, such that the alarm trigger selectively determines between a) when at least a first vital data from the different vital data is abnormal and out of acceptable values, but a second vital data from the different vital data is within a first range of acceptable values, the criterion is met; and b) when the at least first vital data is abnormal and out of the acceptable values, but the ambient data and position data are outside a second range of acceptable values, the criterion is met;

a housing configured to physically store the processor, memory, third network interface, sensor module, data storage device, data storage logic, and the first data access module.

2. The system of claim 1, wherein the computer comprises:
an emergency dispatch module configured to contact an emergency dispatch system; and
a healthcare contact module configured to contact a healthcare provider.

3. The system of claim 1, comprising:
a command module configured to receive third party contact information;
a biographic intake module configured to receive biographic information about the user; and
a third-party contact module configured to send a message to a third party; said message comprising sensor module data and the biographic information of the user.

4. The system of claim 1, wherein:
the third network interface of the health monitor configured to transmit sensor module data to the edge computing device;
the computer comprising a third-party contact module configured to transmit biographic and sensor module data to a third party if the alarm trigger enters an alarm state; and
wherein the alarm trigger is configured to transmit a message to the computer if the received sensor data fails to meet a criterion.

5. The system of claim 1, wherein:
the health monitor comprises an EKG (electrocardiogram) sensor; the EKG sensor configured to measure hearth rhythm of the user; the third network interface of the health monitor configured to transmit EKG sensor data to the edge computing device;
the computer comprises a healthcare contact module configured to contact a healthcare provider if the alarm trigger has entered the alarm state; and
wherein the alarm trigger is configured to transmit a message to the computer and enter an alarm state if the EKG sensor data does not meet a criterion.

6. The system of claim 1, comprising an alarm response module configured to:
present a selection interface to select what sensor module data to share with the computer;
specify a criterion for the sensor data to meet; and
designate an action for the alarm trigger to take if the sensor module data does not meet a criteria.

7. The system of claim 1, wherein:
the data storage logic is configured to invoke an encryption engine to encrypt data to be stored in the data storage device of the health monitor;
the third network interface is configured to transmit sensor module data in an encrypted form;
the edge computing device comprises a second data access module configured to decrypt the sensor module data; and
an alarm trigger is configured to enter an alarm state if the sensor module data does not meet a criterion.

8. The system of claim 1, wherein:
the data storage logic is configured to invoke an encryption engine to encrypt data to be stored in the data storage device of the health monitor;
the third network interface is configured to transmit sensor module data in an encrypted form; and
an alarm trigger is configured to enter an alarm state if the sensor module data does not meet a criterion set by the user.

9. The system of claim 6, wherein the first data access module is configured to request the user provide a credential to access the sensor module data.

10. The system of claim 6, wherein the edge computing device comprises a second data access module configured to request the user present a credential to decrypt the sensor module data.

11. The system of claim 6, wherein the alarm trigger is configured to enter an alarm state if the sensor module data does not meet a criterion set by the user.

12. The system of claim 6, wherein the computer comprises an emergency response dispatch module configured to send a message to an emergency response dispatcher; said message containing a request for emergency assistance, biographic information of the user, location of the user, and sensor module data.

13. The system of claim 6, wherein the computer is configured to send a message to an emergency point of contact; said message containing a request for assistance, biographic information of the user, location of the user, and sensor module data.

14. The system of claim 1, wherein the computer is configured to:
identify a second health monitor physically located within a physical distance threshold of the health monitor; said second health monitor comprising a microprocessor; and
send a message containing a request for assistance, biographic information of the user, location of the user and sensor module data to the second health monitor.

15. The system of claim 1, wherein the edge computing device comprises a biographic intake module configured to generate an account for the user; said account including a userID, username, email address, and phone number.

16. The system of claim 1, comprising:
an alarm trigger configured to enter an alarm state when sensor module data does not meet a criterion; and
an alarm response module configured to request the user select an action for the alarm trigger to take if the alarm trigger enters the alarm state.

17. The system of claim 16, comprising a third-party contact module configured to contact an emergency point of contact if the alarm response module is configured to contact an emergency point of contact and the alarm trigger has entered the alarm state.

18. The system of claim 17, wherein the third-party contact module requires the user provide an approval message before it can send any biographic or sensor module data.

19. The system of claim 17, comprising an emergency dispatch module configured to send a message to an emergency dispatch system; said message comprising sensor module data and biographic information about the user.

20. The system of claim 1, wherein the sensor module of the health monitor comprises a vital sensor.

21. The system of claim 1, wherein the sensor module of the health monitor comprises an environmental sensor.

22. The system of claim 1, wherein the sensor module of the health monitor comprises a position sensor.

23. The system of claim 1, wherein the sensor module of the health monitor comprises a sleep sensor.

24. A method for monitoring a user comprising:
an edge computing device running an operating system and software application; the edge computing device comprising a first network interface;
a computer, independent from the edge computing device, comprising a second network interface receiving information from the edge computing device;
a health monitor, independent from the edge computing device and the computer, wherein the health monitor is a wearable computer configured to attach to a hand, finger, wrist, ankle, or ear of the user; the health monitor:
executing computer readable instructions with a processor;
executing a health application stored in a memory containing tangible non-transitory memory containing the computer readable instructions;
sending and receiving wireless transmissions from a third network interface with the computer and the edge computing device, and contacting a healthcare provider or health dispatch system without interfacing with the computer or the edge computing device when a criterion is not met; wherein the wireless transmissions are sent to the computer, edge computing device, or healthcare provider upon approval of the user only when the criterion is met; wherein when the criterion is not met, the wireless transmissions are sent to the computer, edge computing device, or healthcare provider without the approval of the user;
connecting a sensor module one or more sensors for receiving sensor data, wherein the received sensor data comprises different vital data from the user, ambient data surrounding the user and position data of the user;
a data storage logic electronically storing the sensor data in a data storage device;
a first data access module retrieving the information from the data storage device;
an alarm trigger entering into an alarm state if the criterion is not met; wherein the criterion comprises a combination of several thresholds, about the different vital data, the ambient data and the position data, that needs to be accomplished in order to determine that the criterion was not met, such that the alarm trigger selectively determines between a) when at least a first vital data from the different vital data is abnormal and out of acceptable values, but a second vital data from the different vital data is within a first range of acceptable values, the criterion is met; and b) when the at least first vital data is abnormal and out of the acceptable values, but the ambient data and position data are outside a second range of acceptable values, the criterion is met; and
a housing physically storing the processor, memory, network interface, sensor module, data storage device, data storage logic, and the first data access module.

25. The method of claim 24, comprising:
a graphic user interface displaying information to a user; and
a command module receiving information and commands from the user.

26. The method of claim 24 comprising attaching the health monitor to a human's hand, finger, wrist, ankle, or ear.

27. The method of claim 24 comprising:
receiving the sensor data from a vital sensor;
receiving the sensor data from an environmental sensor;
receiving the sensor data from a position sensor; and
receiving a data feed configured to receive data from an external source.

28. The method of claim 24 comprising sending and receiving communications with Bluetooth or ANT+ technology between the health monitor and the edge computing device.

* * * * *